(12) United States Patent
Fujita et al.

(10) Patent No.: US 6,301,956 B1
(45) Date of Patent: Oct. 16, 2001

(54) HARDNESS TESTER (75) Inventors: Hideto Fujita; Osamu Kudo; Yoshiyuki Fujita; Toyokazu Maeda, all of Kyoto (JP)

(73) Assignees: Edison Hard Co., Ltd.; Shimadzu Corporation, both of Kyoto (JP)

( * ) Notice: Subject to any disclaimer, the term of this patent is extended or adjusted under 35 U.S.C. 154(b) by 0 days.

(21) Appl. No.: 09/458,980

(22) Filed: Dec. 10, 1999

(30) Foreign Application Priority Data

Dec. 14, 1998 (JP) .................................................. 10-354638

(51) Int. Cl.[7] .............................. G01N 3/42; G01N 3/48; B23Q 17/20
(52) U.S. Cl. ......................................... 73/82; 73/78; 73/81
(58) Field of Search .................................... 73/81, 82, 78

(56) References Cited

U.S. PATENT DOCUMENTS 5,133,210 * 7/1992 Lesko et al. .............................. 73/81
5,355,721 * 10/1994 Las Navas Garcia .................... 73/82

* cited by examiner

*Primary Examiner*—Hezron Williams
*Assistant Examiner*—Katina Wilson
(74) *Attorney, Agent, or Firm*—Armstrong, Westerman, Hattori, McLeland & Naughton, LLP (57) ABSTRACT

A hardness tester for a large test material is downsized by shortening a stroke length of the x-y stage. A hardness tester in accordance with the invention transfers the laser irradiating unit 70 two-dimensionally along the X or Y axis and irradiate a laser beam on the material W under test placed on the stage 10. The tester also monitors the laser beam visually and determine a target position to be measured and transfers the monitoring unit 45 to the determined target position along the X or Y axis and monitor the position by means of the monitoring unit 45. If the position does not fall on a boundary between crystals, the loading unit 55 is two-dimensionally transferred and forms a dent on the position by means of the penetrator 55a. An image of the dent is captured by the monitoring unit 45 and the hardness is determined by calculating a diagonal length of the dent by image processing.

9 Claims, 4 Drawing Sheets

HARDNESS TESTER

BACKGROUND OF THE INVENTION AND RELATED ART STATEMENT

This invention relates to a hardness tester, more particularly, to a hardness tester which is preferably used for monitoring and setting a position to be measured on which an indentor bears a load.

Conventionally a well-known hardness tester has an arrangement in which a predetermined load is born on a material under test by an indentor in order to form a dent and hardness of the material is determined by a shape of the dent. With the hardness tester having the above arrangement, as described in Japan Utility Model laid open number 5-45964, the material under test is placed on a stage which can be transferred along the X and Y axes, a position to be measured is determined visually with making use of a microscope arranged above the stage and a dent is formed on the position of the material by an indentor.

The hardness tester having the above arrangement, however, has following problems.

1) In order to determine a position to be measured the stage has to be transferred on an X-Y plane. Then the larger a material under test becomes, the longer the length of transferring the stage becomes. Therefore X and Y stages become larger. The area of transferring the X and Y stages is about 4 times as large as the size of the material under test.
2) Since distance between an indentor and a stage or distance between a microscope and a stage is adjusted by moving a Z stage up and down, it might happen that the hardness of the concave portion can not be measured. In addition, a teaching operation for setting a plurality of positions to be measured becomes complex if the material under test has a convex or concave portion. The conventional teaching operation is follows: Monitor a position to be measured on a material under test with making use of the microscope, and determine and store the position, then detach the object lens of the microscope from the material by lowering the stage to avoid a possible convex portion on the material. Next, transfer the stage along the X and Y axes and monitor a next position to be measured visually and determine the position. And then move the stage upward to a focusing area of the microscope, observe the surface of the material, and determine and store the position.
3) In order to determine a position to be measured, adjust the virtual optical axis of the object lens of the microscope to a target position to be measured by transferring the stage along the X and Y axes. Then focus the microscope on the target position after the object lens is moved to approach the material and determine the target position by monitoring the position on the material. Since the stage is transferred so as to coincide the virtual optical axis of the object lens with the position to be measured visually, it takes long time or it may fail to determine the position to be measured with accuracy.

OBJECT AND SUMMARY OF THE INVENTION

The first object of the present claimed invention is to provide a hardness tester having an arrangement in which a stroke length of the X and Y stages is shortened.

The second object of the present claimed invention is to provide a hardness tester which can measure hardness of a concave portion and which can simplify a teaching operation for setting a plurality of points to be measured on a material under test having a concave or convex portion.

The third object of the present claimed invention is to provide a hardness tester which can indicate a target position to be measured on the material under test by means of a beam of light.

Figure 1:
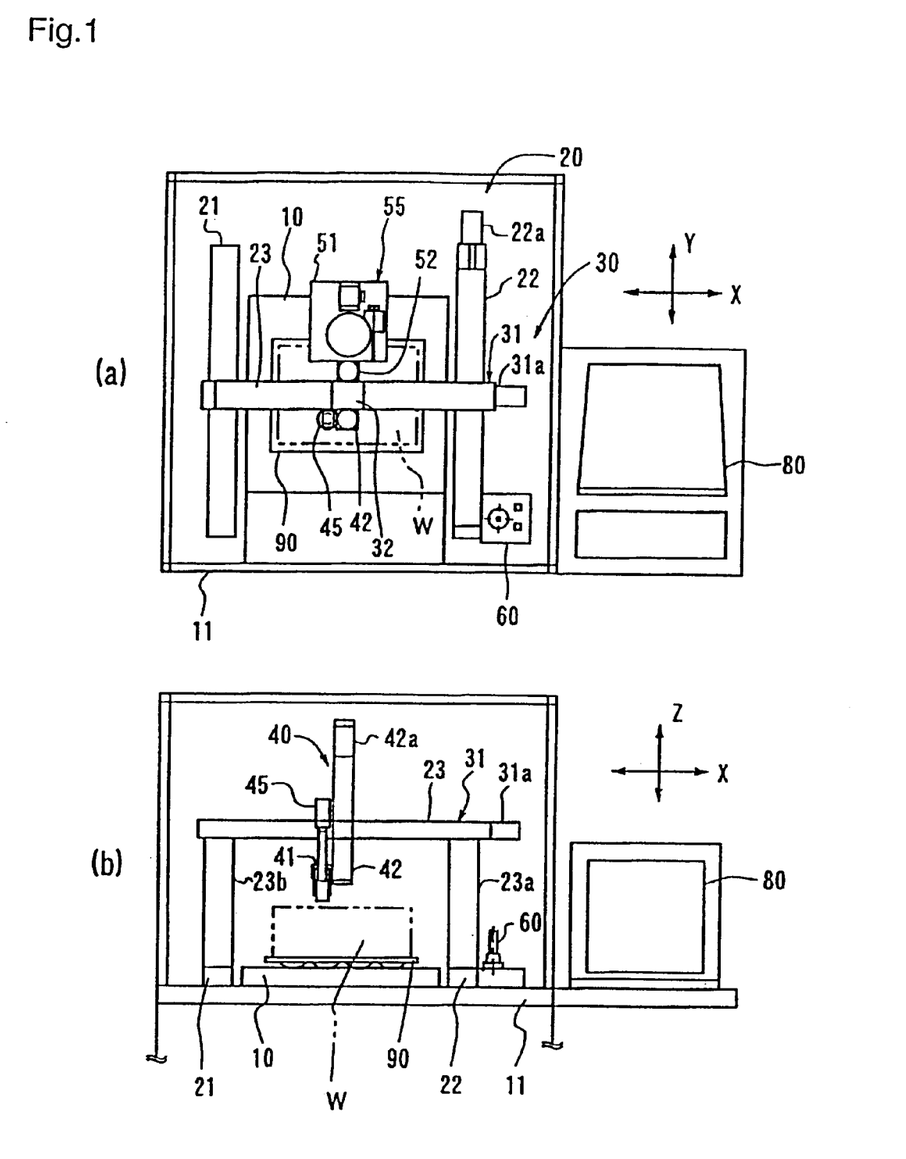
FIG. 1 is a view showing an arrangement of a hardness tester in accordance with one embodiment of this invention, in which (a) shows a plane view of the arrangement and (b) shows a front view thereof.
Figure 2:
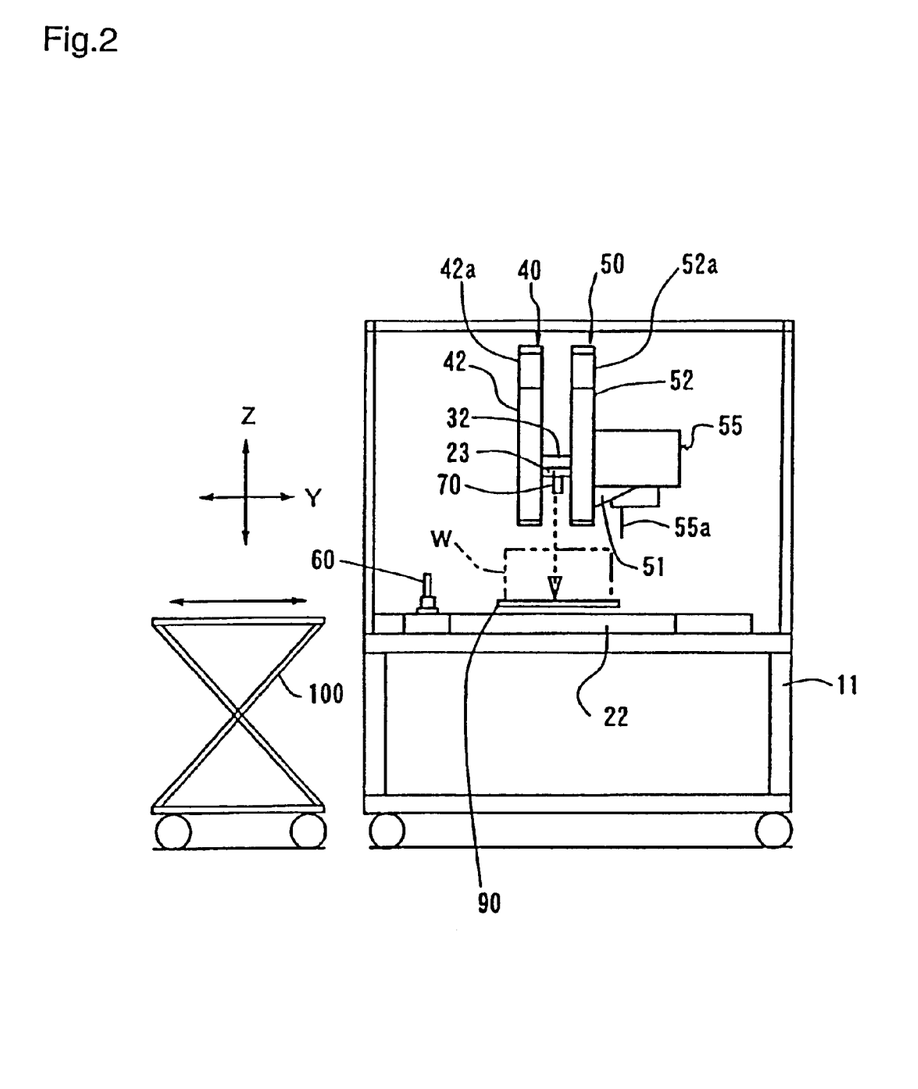
FIG. 2 is a right side view of FIG. 1(b)

In order to accomplish the above-mentioned object the invention has adopted the following structure, which will be explained with referring to FIGS. 1 and 2 showing an embodiment of the invention.

(1) The hardness tester in accordance with claim 1 is characterized by comprising a specimen holder 90 which places a material W under test, an indentor 55a which bears a load on the material W under test, a monitoring unit 45 which monitors the material W under test and a transferring mechanism 20 and 30 each of which holds the indentor and the monitoring unit integrally and which moves the indentor 55a and the monitoring unit 45 two-dimensionally on a plane of the specimen holder 90.

(2) The hardness tester in accordance with claim 2 is characterized by comprising a specimen holder 90 which places a material W under test, a monitoring unit 45 which monitors the material W under test, an indentor 55a which bears a load on the material W under test, a first separating mechanism 40 which moves the monitoring unit 45 away from or close to the specimen holder 90, a second separating mechanism 50 which moves the indentor 55a away from or close to the specimen holder 90 and a control unit 201 which drives the first and second separating mechanism 40 and 50 independently.

(3) The hardness tester in accordance with claim 3 is characterized by comprising a specimen holder 90 which places a material W under test, an indentor 55a which bears a load on the material W under test, a monitoring unit 45 which monitors the material W under test, an irradiating unit 70 which irradiates a beam of light on an arbitrary position of the material W under test and a transferring mechanism 20 and 30 which transfers a position on which the beam of light irradiates two-dimensionally on a plane of the specimen holder 90.

(1) In accordance with the invention of claim 1, the indentor 55a and the monitoring unit 45 are driven by the transferring mechanism 20 and 30 and move two-dimensionally on a plane of the specimen holder 90.

(2) In accordance with the invention of claim 2, the monitoring unit 45 moves apart from or closer to the material W under test by means of the first separating mechanism 40 and the indentor 55a moves apart from or closer to the material W under test by means of the second separating mechanism 50 individually.

(3) In accordance with the invention of claim 3, the irradiating unit 70 moves two-dimensionally on a plane of the specimen holder 90 by means of the transferring mechanism 20 and 30 and the visible ray irradiated from the irradiating unit 70 is irradiated on an arbitrary position on the material W under test.

In order to make it easy to understand the invention for solving the above mentioned problems, the embodiment of the invention is used for explanation, however, the invention is not limited to the arrangement of the embodiment.

As described above, in accordance with the present claimed invention, following effects are produced.

(1) With the invention of claim 1, since the indentor and the monitoring unit are held by the transfer mechanism integrally and they can move on a plane of the specimen holder two-dimensionally, it can prevent the transferring area of the stage from being 4 times as large as a size of the material under test like a conventional hardness tester, thereby to downsize the hardness tester.

(2) With the invention of claim 2, since the indentor and the monitoring unit can move closer to or apart from the material under test independently, it becomes easy to conduct a teaching operation to a material having a convex or concave portion. In addition, since bearing a load on a concave portion can be conducted independently after monitoring the concave portion, it becomes easy to measure hardness of a concave portion, which used to be difficult with a conventional hardness tester.

(3) With the invention of claim 3, since the position to be measured is indicated by a visible ray irradiated on the material by means of an irradiating unit, it becomes easy to determine a position to be measured.

DETAILED DESCRIPTION OF THE PREFERRED EMBODIMENTS

One embodiment of the invention will now be described below with reference to the drawings.

FIGS. 1 and 2 show an arrangement of a hardness tester in accordance with one embodiment of the invention, in which FIG. 1(a) shows a plane view and FIG. 1(b) shows a front view. FIG. 2 shows a right side view of FIG. 1(b). The X, Y and Z axes are taken as shown in FIGS. 1 and 2.

As shown in FIGS. 1 and 2, the hardness tester in accordance with the embodiment comprises a base 11 which is provided with a stage 10, a Y stage guide rail 21 and a Y stage driving unit 22 each of which is arranged on the base 11 and which extends along the Y axis, a U-shaped Y stage 23 which is arranged on the Y stage guide rail 21 and the Y stage driving unit 22 and which moves along the Y axis, an X stage 32 which moves along the X axis and which is driven by an X stage driving unit 31 which is arranged on the Y stage 23 and which extends along the X axis, a first Z stage driving unit 42 which is arranged on the X stage 32 and which drives up and down along the Z axis a first Z stage 41 on which a monitoring unit 45 is mounted, a second Z stage driving unit 52 which is arranged on the X stage 32 and which drives up and down along the Z axis a second Z stage on which a loading unit 55 is mounted, a joystick 60 for instructing each of the stages 23, 32, 41 and 51 to drive, a laser irradiating unit 70 which is arranged on the X stage 32 and which irradiates a beam of marker light which indicates a target position to be measured on a material W under test and a monitor 80 which displays an image monitored by the monitoring unit 45. The material W under test is arranged on a specimen holder 90 having rollers on its base. The specimen holder 90 is fixed to the stage 10 and then measurement is conducted. The specimen holder 90 is conveyed on the stage 10 by a conveying unit 100.

The Y stage driving unit 22 comprises a helical rod (not shown in the drawings) which extends along the Y axis and a Y stage driving motor 22a which drives the helical rod rotatably. A base portion of a leg 23a of the Y stage 23 is helically connected to the helical rod which is rotated by the Y stage driving unit 22. The Y stage 23 is driven along the Y axis when the helical rod is rotated by the Y stage driving motor 22a. The other leg 23b of the Y stage 23 engages with the Y stage guide rail 21 so as to guide the Y stage 23 to move along the Y axis. A Y stage unit 20 comprises the Y stage guide rail 21, the Y stage driving unit 22 and the Y stage 23.

The X stage driving unit 31 comprises a helical rod (not shown in the drawings) which extends along the X axis and a X stage driving motor 31a which drives the helical rod rotatably. The X stage 32 is helically connected to the helical rod which is rotated by the X stage driving unit 31 and driven along the X axis when the helical rod is rotated by the X stage driving motor 31a. An X stage unit 30 comprises the X stage driving unit 31 and the X stage 32.

The first Z stage driving unit 42 comprises a helical rod (not shown in the drawings) which extends along the Z axis and a Z stage driving motor 42a which drives the helical rod rotatably. The first Z stage 41 is helically connected to the helical rod which is rotated by the Z stage driving unit 42 and driven along the Z axis when the helical rod is rotated by the Z stage driving motor 42a. A first Z stage unit 40 comprises the first Z stage 41 and the first Z stage driving unit 42.

The monitoring unit 45 which is driven up and down by the first Z stage unit 40 captures an image of a surface of the material W under test by means of an image capture element such as CCD and displays it on the monitor 80. The monitoring unit 45 is preferably provided with a focus detecting unit, and based on the detected results, the first Z stage 41 is driven up and down to focus on the material W under test. The monitoring unit 45 may be replaced by an optical microscope and the surface of the material W under test may be visually inspected by a person in charge of measurement.

The second Z stage driving unit 52 comprises a helical rod (not shown in the drawings) which extends along the Z axis and a Z stage driving motor 52a which drives the helical rod rotatably. The second Z stage 51 is helically connected to the helical rod which is rotated by the Z stage driving unit 52 and driven up and down along the Z axis when the helical rod is rotated by the Z stage driving motor 52a. A second Z stage unit 50 comprises the second Z stage 51 and the second Z stage driving unit 52. The second Z stage 51 is provided with a loading unit 55 which comprises, as is well-known, an indentor 55a and a weight (not shown in the drawings) which pushes the indentor 55a against the material W under test. The loading unit 55 moves up and down along the Z axis when the helical rod is rotated by the Z stage driving unit 52a.

Figure 3:
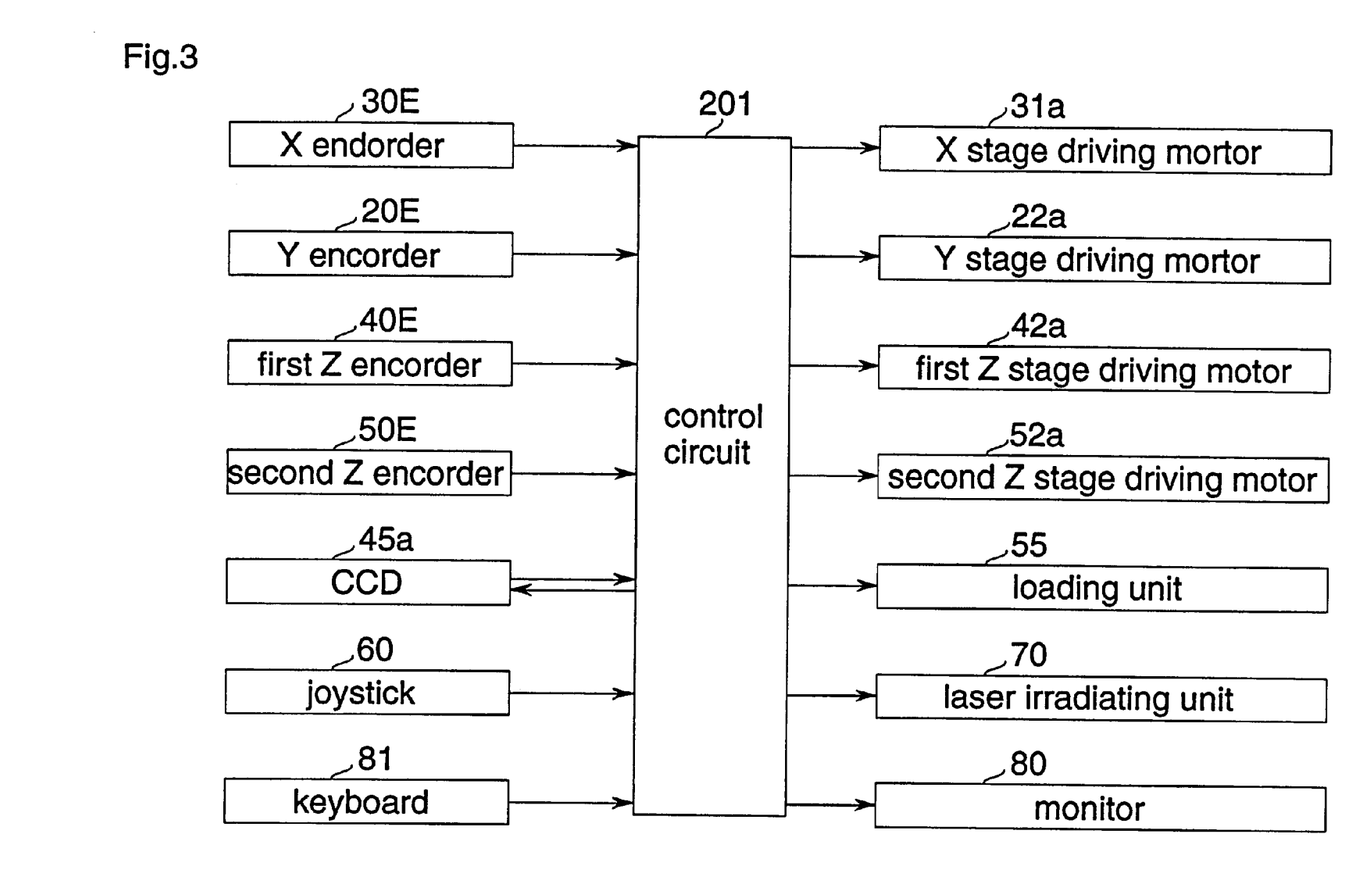
FIG. 3 is a block diagram showing a control system of the hardness tester shown in FIGS. 1 and 2.

FIG. 3 is a diagram showing a control system of the hardness tester. The control system comprises a control circuit 201 having CPU, ROM and RAM. Each of the above-mentioned X stage driving motor 31a, the y stage driving motor 22a, the first and second Z stage driving motors 42a and 52a, the CCD 45a of the monitoring unit 45, the loading unit 55, the laser irradiating unit 70 and the monitor 80 is controlled by the control circuit 201. The control circuit 201 is input a position signal by an X encoder 30E which detects a position of the X stage 32, a Y encoder 20E which detects a position of the Y stage 23, a first Z encoder 40E which detects a position of the first Z stage 41 and a second Z encoder 50E which detects a position of the second Z stage 51. The control circuit 201 is also connected to the above-mentioned joystick 60 or a key board 81. The control circuit 201 stores a position signal taken through a teaching operation and calculates a target position of the monitoring unit 45 or the loading unit 55 by means of the position signal, which will be described later. In addition, hardness is found by calculating a diagonal length of a dent by 18 means of an image processing, which will be described later.

An operation of the embodiment will now be described. First, place the material W under test on the specimen holder 90, convey the specimen holder 90 on the stage 10 by means of the conveying unit 100 and fix it thereto. Irradiate a beam of marker light from the laser irradiating unit 70. Position each of the X and Y stages 32, 23 by operating the joystick 60 so that the beam of marker light irradiates a desired position on the material W under test. At this time the laser irradiating unit 70 should be kept apart enough from the material W under test to avoid colliding with a convex portion of the material W under test if the material W under test has a convex or a concave portion. Optical system of the laser irradiating unit 70 is so arranged that a diameter of a spot made by the beam of marker light on the material W under test is approximately 1 mm. A person in charge of measurement determines a target position to be measured visually by means of the marker light. Then the person instructs to store the position by operating the joystick 60 and each of the position signal which is taken into the control circuit 201 from the X and Y encoders 30E and 20E is stored in a memory unit (not shown in the drawings). The above operation is conducted as a teaching operation to each of a plurality of target positions to be measured.

Next, drive the X and y stages 32, 23 so as to make the position to which the teaching operation is conducted coincide with the optical axis of the monitoring unit 45. The monitoring unit 45 and the laser irradiating unit 70 are integrally arranged with the X stage 32 and position of relative relationship between the monitoring unit 45 and the laser irradiating unit 70 in an x-y coordinate system has already been publicly known. The target position of the optical axis of the monitoring unit 45 is therefore calculated based on the target position to be measure which is determined and stored by means of the irradiating light and the position of relative relationship between the optical axis of the monitoring unit 45 and the laser irradiating unit 70, thereby to position the monitoring unit 45 with accuracy.

Drive the X and Y stages 32, 23 so that the monitoring unit 45 coincide with the first position to be measured. Capture an image of the first position to be measured with the CCD 45a of the monitoring unit 45 and display the image on the monitor 80. Then judge whether the position is suitable for a position to be measured or not. If suitable, store the position as the first position to be measured into the memory unit. In this case, store each of the position signals from the X and Y encoders 30E and 20E into the memory unit. If the monitored position falls on a boundary of crystal particles, the position is not suitable for a position to be measured. Then change the position to be measured to another position by driving the X and Y stages 32, 23 with a joystick 60. If the position is suitable for a position to be measured, store the position by operating the joystick 60 and store the position signal from the X and Y encoders 30E and 20E. This process is conducted to all of the other positions to be measured, then a teaching operation to all positions to be measured is completed.

The monitoring unit 45 and the loading unit 55 are integrally held by the X stage 32 and position of relative relationship between the monitoring unit 45 and the loading unit 55 in an X-Y coordinate system has already been publicly known. As a result, based on the position in the X-Y coordinates stored as an appropriate position to be measured by means of the above-mentioned teaching operation and the relative relationship between the optical axis of the monitoring unit 45 and the indentor 55a of the loading unit 55, a position to which the indentor 55a is supposed to bear a load can be calculated and the indentor 55a can be positioned at the position with accuracy. After the teaching operation to a plurality of points is completed as mentioned above, hardness of the material W is actually measured to find.

First, put the indentor 55a to face to the first position to be measured by transferring the X and Y stages 32, 23 and then lower the loading unit 55 to a predetermined height by means of the second Z stage driving unit 52 so that the indentor 55a makes contact with the surface of the material W under test. With keeping the above state, form a dent on the surface of the material W under test by applying the weight which is built-in the loading unit 55 to the indentor 55a. After the dent is formed, rise the loading unit 55 by means of the second Z stage driving unit 52 and transfer the X and Y stages 32, 23 so that the indentor 55a faces to the next position to be measured. And the same procedure is conducted so as to form a dent on the material W under test by means of the indentor 55a. Repeat the above procedure until a dent is formed to each of the plurality of positions which have been predetermined by means of the teaching operation.

Next, capture images of each of the dents formed on a plurality of positions with the CCD 45a of the monitoring unit 45. Then provide image processing to these images and calculate the hardness of each position using the diagonal length of each dent. In order to find the hardness as mentioned above, first, transfer the X and Y stages 32, 23 so that the optical axis of the monitoring unit 45 faces to the first position to be measured. Then set the monitoring unit 45 at a predetermined height by means of the first Z stage driving unit 42 so as to focus the monitoring unit 45 on the dent. With this condition, store an image captured by the CCD 45a, convert the image into a digital value, and store the digitalized image into a buffer memory. After the process of capturing the image of the first position is finished, transfer the X and Y stages 32, 23 so as to face the monitoring unit 45 to the second position to be measured. Then capture an image of the dent formed on the second position and store the digital image into the memory. Conduct this process repeatedly to all of the other positions to be measured, then store each of the digital images of the dent formed on a plurality of positions to be measured. A predetermined image processing is provided to every stored images, calculate each of the diagonal lengths of the dents formed on the positions and find the value of hardness at the positions based on the load born by the indentor 55a and the diagonal length.

In accordance with the hardness tester having the above arrangement, the monitoring unit 45 and the loading unit 55 can be moved on an X-Y plane and there is no need of moving the material W under test. It is therefore enough for the stage 10 just to have the same size as that of the material W under test, thereby to downsize the hardness tester.

For a material W under test having a concave or convex portion on the surface thereof, if the laser irradiating unit 70 is arranged apart enough from the material W under test, the laser irradiating unit 70 can be transferred on an X-Y plane by means of the X and Y stages 32, 23 without moving up or down the laser irradiating unit 70. It is therefore possible to shorten the time needed for teaching operation conducted to the material W under test having a concave or convex portion. Since it is possible to determine the position to be measured roughly by visual observation of a beam of marker light irradiated on the material W under test, it becomes easy to determine a target position to be measured when compared with a conventional case in which a virtual optical axis of an object lens is first set on a surface of the material W under test and then determine the position visually.

Since the monitoring unit 45 is mounted on the first Z stage unit 40 and the loading unit 55 is mounted on the second Z stage unit 50 respectively and they can be moved up and down along the Z axis independently, it becomes easy to conduct a teaching operation of the position to be measured for a material W under test having a concave or convex portion. This also makes it possible to measure hardness of a concave portion of the material W under test. In other words, move the optical axis of the monitoring unit 45 to face to the position to be measured by means of the X and Y stage units 30, 20 and lower the monitoring unit 45 along the Z axis by mean of the first Z stage unit 40. More specifically, insert a lens tube of the monitoring unit 45 into a concave portion which is to be measured on the surface of the material W under test and focus the monitoring unit 45 on the position. If the position is suitable for a position to be measured, store the position. Then rise the monitoring unit 45 and calculate the X-Y coordinate position of the indentor 55a based on the stored position. Transfer the indentor 55a of the loading unit 55 to the X-Y coordinate position by means of the X and Y stage units 30, 20 so that the indentor 55a faces to the position to be measured on the concave position. Move the indentor 55a so that the indentor 55a makes contact with the position to be measured of the material W under test by means of the second Z stage unit 50 and form a dent on the material W under test by means of the indentor 55a with applying a load thereto. As mentioned above, since the monitoring unit 45 and the loading unit 55 are transferred on the X-Y plane together while they can move individually along the Z axis, it is possible to measure the hardness of the concave portion, which has conventionally been difficult.

In the above arrangement, the monitoring unit 45 may comprise an optical microscope, instead of CCD 45a. In this case, the diagonal length of the dent is measured visually through the optical microscope, not by means of image processing. In addition, instead of the above procedure which comprises: first determine a plurality of target positions to be measured, obseve the target positions one by one and determine a plurality of positions to be measured, form a dent on each of the positions, capture each of the images of the dents one after another, and find hardness, the following procedure may be used, which comprises: visually inspect and determine one target position to be measured, form a dent on the position, capture the image of the dent and calculate the hardness of the position by capturing the image, and the procedure is repeated to other target positions. Further, instead of arranging the laser irradiating unit 70 on the X stage 32 and transferring it two-dimensionally, a scanning mechanism may be provided which scans a beam of light irradiated from a fixed laser irradiating unit 70 if the material W to be bested is not so big. In this case, the scanning mechanism functions as a transferring mechanism of the beam of light.

Figure 4A:
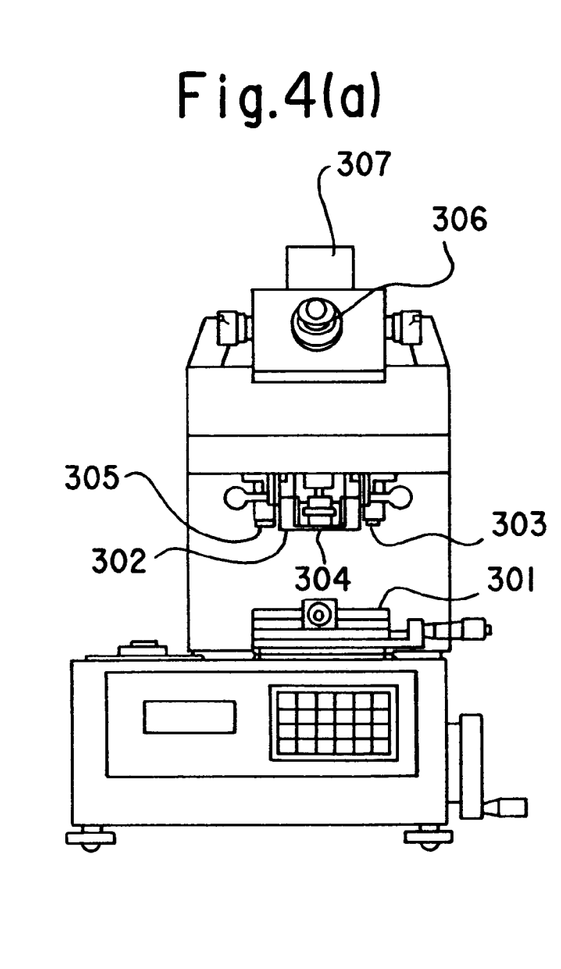
FIG. 4 is another embodiment of the hardness tester, in which (a) shows a front view and (b) shows a side view.
Figure 4B:
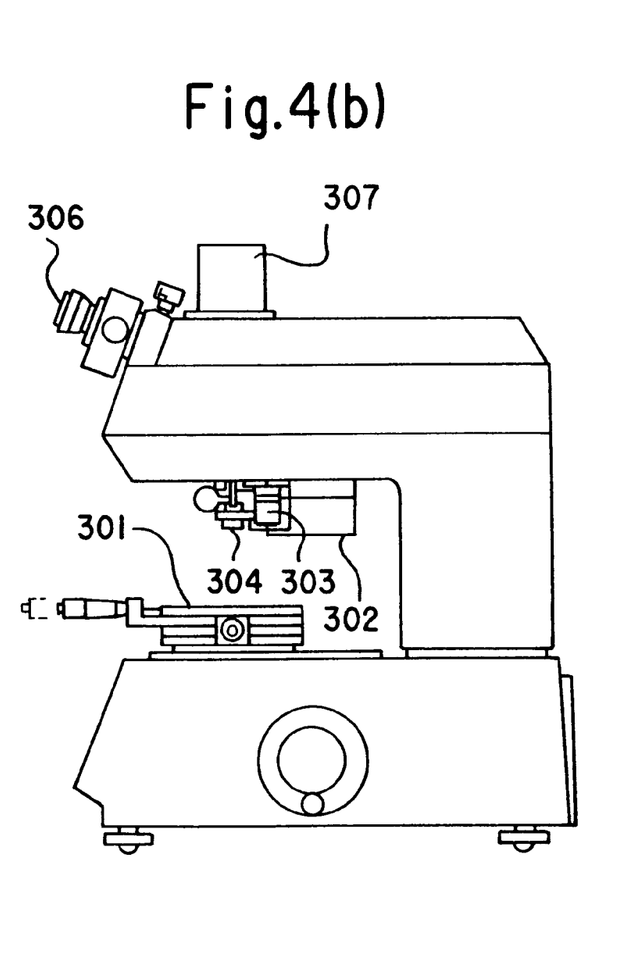

FIG. 4 shows another embodiment of the invention, wherein a laser irradiating unit in accordance with the invention is provided to a conventional hardness tester and this is to visualize a target position to be measured by means of a beam of marker light. As shown in FIG. 4, a material under test is placed on the X-Y-Z stage 301 and a revolver 302 which is rotatably arranged upward to face to the stage 301 is provided with an object lens 303, an indentor 304 and a laser irradiating unit 305. The numeral 306 represents an ocular which constitutes a microscope together with the object lens 303, and 307 represents a CCD image capture element which captures images of the surface of the material under test.

A process to measure hardness of the material under test by means of the hardness tester shown in FIG. 4 will now be explained. Rotate the revolver 302 so as to face the laser irradiating unit 305 to the material under test and irradiate a spotlight of a laser beam on the material under test. A person in charge of measurement moves the X-Y-Z stage 301 with visually observing the spotlight on the material under test so that the laser beam irradiates on the target position to be measured. After the position to be measured is determined, rotate the revolver 302 so as to face the object lens 303 to the target position, focus the microscope on the position and observe the surface of the material under test. If the position does not fall on a boundary of crystal particles, rotate the revolver 302 so that the indentor 304 faces to the position to be measured and form a dent by means of the indentor 304.

In accordance with the hardness tester shown in FIG. 4, since the target position to be measured is indicated by a visible ray, it becomes extremely easy to determine a target position.

The above embodiment corresponds to the claims, in which the X stage unit 30 and the Y stage unit 20 correspond to a transferring mechanism, the first Z stage unit 40 corresponds to a first separating mechanism and the second Z stage unit 50 corresponds to a second separating mechanism independently.

What is claimed is:

1. A hardness tester comprising:
   a specimen holder which places a material under test,
   an indentor which bears a load on said material under test,
   a monitoring unit which monitors said material under test, and
   a transferring mechanism which holds said indentor and said monitoring unit integrally and which transfers said indentor and said monitoring unit two-dimensionally on a plane of said specimen holder.

2. The hardness tester as recited in claim 1, further comprising:
   an irradiating unit which irradiates a beam of light on an arbitrary position of said material under test and that said transferring mechanism transfers a position on which said beam of light irradiates two-dimensionally on a plane of said specimen holder.

3. The hardness tester, as recited in claim 6, wherein said transferring mechanism holds said indentor, said monitoring unit and said irradiating unit integrally.

4. The hardness tester, as recited in claim 2, further comprising:
   an irradiating unit which irradiates a beam of light on an arbitrary position of said material under test and a transferring mechanism which transfers a position on which said beam of light irradiates two-dimensionally on a plane of said specimen holder.

5. A hardness tester comprising
   a specimen holder which places a material under test,
   an indentor which bears a load on said material under test,
   a monitoring unit which monitors said material under test, a first separating mechanism which moves said monitoring unit away from or close to said specimen holder, a second separating mechanism which moves said indentor away from or close to said specimen holder, and a control unit which drives said first and second separating mechanism independently.

6. The hardness tester, described in claim 1, further comprising:

a first separating mechanism which moves said monitoring unit away from or close to said specimen holder, a second separating mechanism which moves said indentor away from or close to said specimen holder and a control unit which drives said first and second separating mechanism independently, and an irradiating unit which irradiates a beam of light on an arbitrary position of said material under test and that said transferring mechanism transfers a position on which said beam of light irradiates two-dimensionally on a plane of said specimen holder.

7. A hardness tester comprising:

a specimen holder which places a material under test, an indentor which bears a load on said material under test, a monitoring unit which monitors said material under test, an irradiating unit which irradiates a beam of light on an arbitrary position of said material under test and a transferring mechanism which transfers a position on which said beam of light irradiates two-dimensionally on a plane of said specimen holder.

8. The hardness tester, as recited in claim 5, wherein a direction of movement by the first and second separating mechanism makes a right angle to a direction of a surface of said specimen holder.

9. The hardness tester as recited in claim 5, further comprising:

a first separating mechanism which moves said monitoring unit away from or close to said specimen holder, a second separating mechanism which moves said indentor away from or close to said specimen holder and a control unit which drives said first and second separating mechanism independently.

* * * * *

UNITED STATES PATENT AND TRADEMARK OFFICE
CERTIFICATE OF CORRECTION

PATENT NO.   : 6,301,956 B1
DATED        : October 16, 2001
INVENTOR(S)  : Fujita et al.

It is certified that error appears in the above-identified patent and that said Letters Patent is hereby corrected as shown below:

Column 8,
Lines 56-62, amend claims 4 and 9 as follows:

4.   The hardness tester, as recited in claim [2]5, further comprising:
an irradiating unit which irradiates a beam of light on an arbitrary position of said material under test and a transferring mechanism which transfers a position on which said beam of light irradiates two-dimensionally on a plane of said specimen holder.

Column 10,
Lines 13-20, amend as follows:

9.   The hardness tester as recited in claim [5]1, further comprising;
a first separating mechanism which moves said monitoring unit away from or close to said specimen holder, a second separating mechanism which moves said indentor away from or close to said specimen holder and
a control unit which drives said first and second separating mechanism independently.

Signed and Sealed this

Seventh Day of May, 2002

*Attest:*

JAMES E. ROGAN
*Attesting Officer*   *Director of the United States Patent and Trademark Office*